(12) United States Patent
Suzuki et al.

(10) Patent No.: US 9,022,597 B2
(45) Date of Patent: May 5, 2015

(54) LINE LIGHT IRRADIATION DEVICE AND MANUFACTURING METHOD THEREOF

(75) Inventors: Ryoko Suzuki, Kyoto (JP); Kenji Miura, Uji (JP)

(73) Assignee: CCS Inc., Kyoto-shi (JP)

( * ) Notice: Subject to any disclaimer, the term of this patent is extended or adjusted under 35 U.S.C. 154(b) by 94 days.

(21) Appl. No.: 13/978,522

(22) PCT Filed: Feb. 16, 2012

(86) PCT No.: PCT/JP2012/053664
§ 371 (c)(1),
(2), (4) Date: Jul. 5, 2013

(87) PCT Pub. No.: WO2012/120987
PCT Pub. Date: Sep. 13, 2012

(65) Prior Publication Data
US 2013/0329436 A1    Dec. 12, 2013

(30) Foreign Application Priority Data

Mar. 4, 2011 (JP) ................................. 2011-048237

(51) Int. Cl.
*F21S 4/00* (2006.01)
*F21V 17/16* (2006.01)
*G01N 21/88* (2006.01)
(Continued)

(52) U.S. Cl.
CPC ........... *F21V 17/16* (2013.01); *Y10T 29/49872* (2015.01); *F21S 4/008* (2013.01); *F21V 15/013* (2013.01); *G01N 21/8806* (2013.01); *F21Y 2101/02* (2013.01); *F21V 5/043* (2013.01)

(58) Field of Classification Search
CPC ... G01N 21/8806; F21V 17/16; F21V 15/013; F21V 5/043; Y10T 29/49872; F21Y 2101/02; F21S 4/008

USPC .............. 362/311.02, 555, 33, 652, 223, 224, 362/225, 217.12, 217.13; 29/451
See application file for complete search history.

(56) References Cited

U.S. PATENT DOCUMENTS

| 7,300,179 B1 * | 11/2007 | LaDuke et al. ............... 362/253 |
| 2002/0044456 A1 | 4/2002 | Balestriero et al. |
| 2007/0217197 A1 | 9/2007 | Palatzky et al. |

FOREIGN PATENT DOCUMENTS

| EP | 1182396 A1 | 2/2002 |
| JP | 01280571 A | 10/1989 |

(Continued)

OTHER PUBLICATIONS

ISA European Patent Office, Extended European Search Report in European Patent Application No. 12755151, Aug. 19, 2014, 6 pages.

(Continued)

*Primary Examiner* — Anh Mai
*Assistant Examiner* — Glenn Zimmerman
(74) *Attorney, Agent, or Firm* — Alleman Hall McCoy Russell & Tuttle LLP (57) ABSTRACT

The present invention includes: a casing having a bottom wall part and a pair of side wall parts extending upward from this bottom wall part; a rod-shaped lens provided above an LED substrate and along a longitudinal direction inside the casing; and a fixing mechanism for fixing the lens to the pair of side wall parts. The fixing mechanism includes: upwardly facing surfaces longitudinally extending along an inner surface of the side wall parts; downwardly facing surfaces longitudinally extending along side peripheral surfaces of the lens; a concave groove longitudinally extending above the upwardly facing surface on the inner surface of each of the side wall parts; and elastic bodies fitting into the concave grooves to be in contact with the side peripheral surfaces of the lens in a state that the downwardly facing surfaces are in contact with the upwardly facing surfaces.

9 Claims, 7 Drawing Sheets

(51) Int. Cl.
   *F21V 15/01* (2006.01)
   *F21Y 101/02* (2006.01)
   *F21V 5/04* (2006.01)

(56) References Cited

FOREIGN PATENT DOCUMENTS

| JP | 01311759 | A | 12/1989 |
| JP | 06135052 | A | 5/1994 |
| JP | 11072734 | A | 3/1999 |
| JP | 2010112939 | A | 5/2010 |

OTHER PUBLICATIONS

Japanese Patent Office, International Search Report of PCT/JP2012/053664, May 15, 2012, WIPO, 4 pages.

\* cited by examiner

LINE LIGHT IRRADIATION DEVICE AND MANUFACTURING METHOD THEREOF

TECHNICAL FIELD

The present invention relates to a light irradiation device capable of irradiating, for example, line-shaped light using a plurality of LEDs, and in particular to a light irradiation device appropriately used for inspection such as checking presence or absence of a crack in a predetermined irradiation region of a work piece (product), reading a mark and the like.

BACKGROUND ART

Conventionally, as disclosed in Patent Literature 1, there has been considered as a line light irradiation device that includes a long-size shaped LED substrate having a plurality of LEDs mounted thereon, a casing for accommodating this LED substrate, and a round bar shaped rod lens fixed to the casing for condensing light rays from the plurality of LEDs to a line shaped one. Specifically, a structure for fixing the rod lens positioned above the LEDs is configured of projections corresponding to an outer diameter of the rod lens and buffer members provided between the projections and the rod lens to thereby prevent looseness of the rod lens.

However, the line light irradiation device described in this Patent Literature 1 is to be assembled by inserting the rod lens into the casing along a longitudinal direction while the casing is in a state of fixing the buffer members to the projections. If so, there arises a problem that it is hard to insert the rod lens into the casing due to a slip resistance between the buffer members and the rod lens. This problem becomes more remarkable as a longitudinal size of the casing becomes larger or longitudinal size of the rod lens becomes longer.

CITATION LIST

Patent Literature

Patent Literature 1: JP-A2010-112939

SUMMARY OF INVENTION

Technical Problem

Therefore, the present invention has been made in order to solve the above problem and a main object thereof is to fix a lens to a casing and not only prevent looseness thereof but also facilitate assembly.

Solution to Problem

Accordingly, a line light irradiation device according to the present invention is characterized by including: an integrally molded casing having a bottom wall part extending in a longitudinal direction and a pair of side wall parts extending upward from both sides in the longitudinal direction of this bottom wall part; an LED substrate provided on the bottom wall part of the casing; a rod-shaped lens provided above the LED substrate along the longitudinal direction inside the casing; and a fixing mechanism for fixing the lens to the pair of side wall parts, wherein the fixing mechanism includes: a respective upwardly facing surface extending in the longitudinal direction along an inner surface of each of the side wall parts; a respective downwardly facing surface extending in the longitudinal direction along each side peripheral surface of the lens; a respective concave groove extending along the longitudinal direction above the upwardly facing surface on the inner surface of each of the side wall parts; and a respective elastic body detachably provided in each concave groove and fitting into each concave groove to be in contact with a corresponding side peripheral surface of the lens in a state that the downwardly facing surfaces are in contact with the upwardly facing surfaces to thereby press the downwardly facing surfaces against the upwardly facing surfaces. Here, the upwardly facing surface may just be a surface having an upward component and is a concept including an inclined surface or a curved surface besides a substantially horizontal surface. Further, the downwardly facing surface may just be a surface having a downward component and is a concept including an inclined surface or a curved surface besides a substantially horizontal surface. At this time, it is desirable that the upwardly facing surface and the downwardly facing surface may be in surface-contact.

With a configuration like this, the fixing mechanism includes the upwardly facing surface provided in the inner surface of each of the side wall parts and the downwardly facing surface provided in the side peripheral surface of the lens, and the lens can be fixed to the casing while positioning the lens to the casing in the vertical direction by contacting between these upwardly facing surface and downwardly facing surface. Further, since the fixing mechanism includes the concave grooves and the elastic bodies which are fit to these concave grooves to press the side peripheral surfaces of the lens, the lens can be fixed to the casing while preventing the looseness of the lens with respect to the casing. Moreover, after contacting the downwardly facing surface with the upwardly facing surface, the lens can be pressed and fixed to the casing only by fitting the elastic bodies in the concave grooves, whereby assembly can be facilitated. At this time, since the elastic body is not fit in the concave groove at the time of attaching the lens to the casing, the operation of attaching the lens to the casing can be facilitated. In addition, since the casing is integrally molded, not only the number of assembling man-hours can be reduced but also heat dissipation performance of the casing can be improved.

In order to prevent the elastic body from being detached from the concave groove in a state the elastic body is fit to the concave groove, it is desirable that a shortest distance between the upper end portion of the concave groove and the side peripheral surface of the lens is smaller than a width size in the natural state of the elastic body.

In order to reduce the number of manufacturing man-hours of the casing and to be able to appropriately use the casing in the line light irradiation device, it is desirable that the casing is integrally formed by extrusion molding or pultrusion molding.

It is desirable that the upwardly facing surface is formed of an upper surface of a projected rim part extending in the longitudinal direction along the inner surface of each of the side wall parts and the downwardly facing surface is formed of a lower surface of each of two notch portions which are provided along the side peripheral surface of the lens and symmetrically formed with respect to the optical axis. With this configuration, even in the case of using an integrally molded lens, the lens can be positioned. Further, since only notch portions are provided it may be sufficient to only perform, for example, a process such as cutting the existing lens, and as such the processing is easy and a manufacturing cost can also be made inexpensive.

In order to perform the horizontal positioning of the lens to the LED mounted on the LED substrate at the same time of fixing the lens to the casing, it is desirable that the projected rim part has the inward surface which is substantially perpendicular to the upwardly facing surface, the notch portion has an outward surface which is substantially perpendicular to the downwardly facing surface, the inward surface of the projected rim part is in contact with the outward surface of the notch portion, and the upwardly facing surface of the projected rim part is in contact with the downwardly facing surface of the notch portion. With this configuration, the horizontal positioning of the lens can be performed by the inward surface of the projected rim part and the downwardly facing surface of the notch, and the other positioning structure for positioning the casing and lens can be made unnecessary to thereby simplify the configuration of the line light irradiation device.

It is desirable that the space between the upper side portions above the projected rim parts of the pair of side wall parts is configured to be larger than the outer diameter of the lens. With this configuration, the lens can be accommodated from an upper opening of the case and the assembling work can be facilitated.

Further, as a manufacturing method particular to the above-mentioned line light irradiation device, it is characterized by including: a lens accommodation process of accommodating the lens in the casing; and an elastic body fitting process of fitting the elastic body into the concave groove after the lens accommodation process.

Here, in order to facilitate the work of fitting the elastic body into the concave groove and improve the workability, it is desirable that the elastic body fitting process fits the elastic body into the concave groove using a jig after the elastic body fitting process arranges the elastic body in the gap between the upper end portion of the concave portion and the side surface of the lens.

It is desirable that the jig includes the jig main body having the tip surface which is in contact with the elastic body and the guide part which is provided in the jig main body and to be in contact with the upper surface of the casing, and, by bringing the guide part into contact with the upper surface of the casing, the tip surface of the jig main body is in contact with the elastic body to thereby fit the elastic body to the concave groove. With this configuration, since the tip surface of the jig main body renders the elastic body to be fit into the concave groove in a state that the guide part is in contact with the upper surface of the casing, the elastic body can be surely fit into the concave groove and there arises no problem such that the elastic body is destroyed due to a power at the time of fitting added too excessively.

More specifically, it is desirable that the jig main body is the main body roller which is rotatable about the rotation axis, the guide part is the guide roller coaxially provided with the rotation axis of the roller, and by rolling the guide roller while contacting with the upper surface of the casing in a state that one side surface of the main body roller is along the inner side surface of the casing, the side peripheral end surface of the main body roller is in contact with the elastic body to thereby fit the elastic body into the concave groove. With a configuration like this, by only rolling the jig and the guide roller thereof on the upper surface of the casing, the elastic body can be fit into the concave groove.

Advantageous Effects of Invention

According to the present invention like this, the rod lens can be fixed to the casing, and while not only preventing looseness thereof but also facilitating the assembling work, a light transmission portion of the rod lens can be prevented from being damaged.

REFERENCE CHARACTER LIST

1 ... Line light irradiation device
C ... Optical axis
2 ... Casing
21 ... Bottom wall part
22, 23 ... Side wall part
3 ... LED substrate
4 ... Rod lens
5 ... Fixing mechanism
51 ... Projected rim part
51$a$ ... Upwardly facing surface
51$b$ ... Inward surface
52 ... Notch portion
52$a$ ... Downwardly facing surface
52$b$ ... Outward surface
53 ... Concave groove
54 ... Elastic body

DESCRIPTION OF EMBODIMENTS

Next, one embodiment of a line light irradiation device 100 according to the present invention is described referring to the drawings.

The line light irradiation device 100 according to the present embodiment is adapted to irradiate line shaped light to, for example, a predetermined irradiation region of an inspection object (work) and it is used for such as a product inspection system, etc., which photographs the predetermined irradiation region with a photographing device (not shown), captures obtained image data with an image processing device (not shown) to perform an automatic inspection of checking the presence or absence of a defect such as, e.g., a crack or dirt, a foreign matter in liquid, or mark inspection.

Figure 1:
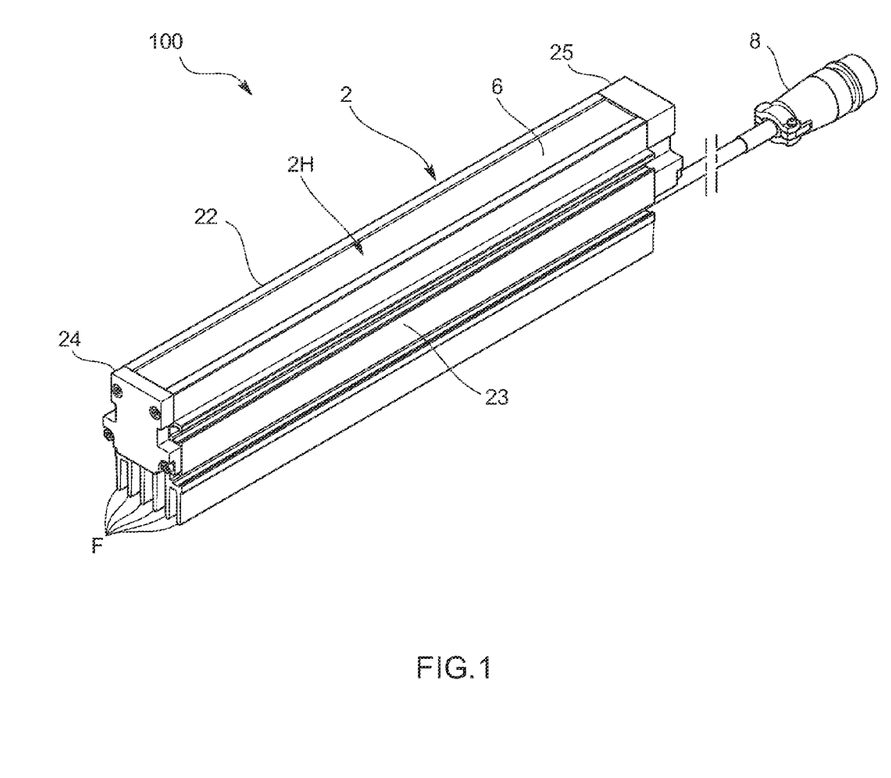
FIG. 1 is a perspective view showing a line light irradiation device of the present embodiment.
Figure 2:
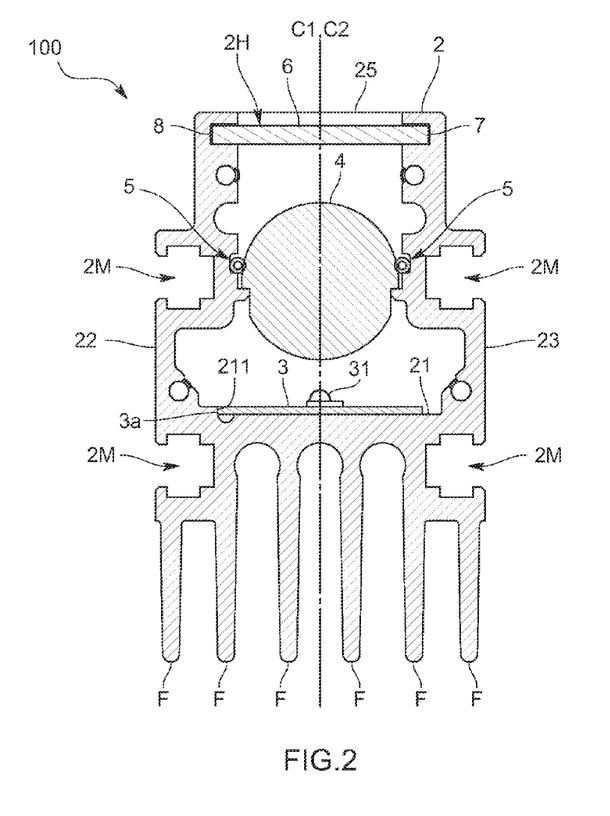
FIG. 2 is a cross sectional view of the line light irradiation device of the same embodiment.

Specifically, as shown in FIGS. 1 and 2, this device is provided with: a casing 2; an LED substrate 3 accommodated in the casing 2; a rod lens 4 which is a rod-like lens accommodated in the casing 2; and a fixing mechanism 5 for fixing the rod lens 4 to the casing 2.

As shown in FIG. 2, the casing 2 is adapted to accommodate the LED substrate 3, rod lens 4, and a light transmission plate 6 such as a diffusion plate and a protection cover. Specifically, the casing 2 is a long-sized metal one and is formed in a generally U-character shape in section perpendicularly intersecting in a longitudinal direction (extending direction), and includes a bottom wall part 21 extending in the longitudinal direction and a pair of left and right side wall parts 22 and 23 extending upward from longitudinal-directed both sides of this bottom wall part 21. This casing 2 is an integrally formed one by extrusion molding or pultrusion molding, and on a back surface of the bottom wall part 21, there are provided plural sheets of radiator fins F along the longitudinal direction for radiating heat to the outside from the LED substrate 3. Further, in the bottom wall part 21 and left and right side wall parts 22 and 23, there are provided attachment grooves 2M for attaching the line light irradiation device 100 to an external member (e.g., rack, etc.). Further, front and rear side walls 24 and 25 are fixed to one end and the other end in the longitudinal direction of the casing 2 with screws and the like. Thus, the casing 2 is formed with a generally rectangular shaped light outgoing port 2H in the upper part thereof. In addition, an electrical cable 8 is extended from the rear side wall 25 for supplying electric power to the LED.

The LED substrate 3 is a long-sized substrate mounting a plurality of LEDs 31. Specifically, the LED substrate 3 is formed by machine-mounting the plurality of LEDs 31 to be arranged in one or more lines (one line in FIG. 2) in a shorted side direction on a surface of a long-sized print circuit board so as to align optical axes C1 thereof in a generally constant direction to be in a straight line state in a longer side direction. The LEDs 31 are surface-mount type ones of arranging LED elements in a center of a package which forms, for example, a thin rectangular plate shape. Such LEDs 31 are arranged so as to arrange the LED elements, for example, at predetermined intervals in the longer side direction and shorter side direction, respectively.

This LED substrate 3 is fixed to an upper surface of the bottom wall part 21 of the casing 2. And regarding this LED substrate 3, a longer side direction side surface 3a of the LED substrate 3 contacts with a substrate contacting surface 211 which is a substrate positioning structure provided along the longitudinal direction on the bottom wall part 21, and the LED substrate 3 is thereby positioned to the casing 2 in a lateral direction (a direction perpendicular to the longitudinal direction).

The rod lens 4 is a condenser lens of a generally circular shape with an equal cross-section having a generally same length as a length of each of the left and right side walls 22 and 23 of the casing 2. This rod lens 4 is provided along the longitudinal direction above the LED substrate 3 inside the casing 2 and is fixed to be in a predetermined position with respect to the plurality of LEDs 31 mounted on the LED substrate 3 by a fixing mechanism 5 to be described later. Specifically, the rod lens 4 is fixed by the fixing mechanism 5 in a manner such that an optical axis C2 of the rod lens 4 coincides with the optical axes C1 of the plurality of LEDs 31 and that the rod lens 4 is spaced a predetermined distance with respect to the plurality of LEDs 31. In addition, the light transmission plate 6 such as a diffusion plate and a protection cover is provided in a front (upper portion) in a light outgoing side of the rod lens 4, and since this light transmission plate 6 is thermally expanded, it is attached by a slide groove 7 with a slight play formed in an inner surface of each of the left and right side walls 22 and 23.

Figure 3:
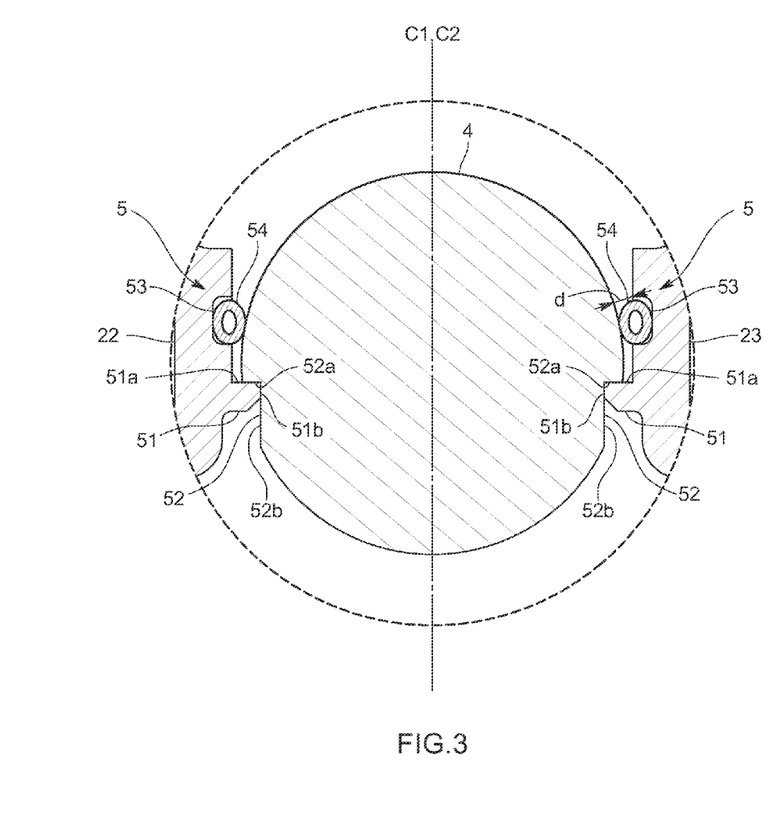
FIG. 3 is a partially expanded sectional view showing details of a fixing mechanism of the same embodiment.

As shown in FIG. 3, the fixing mechanism 5 is intended to fix the rod lens 4 to the pair of left and right side wall parts 22 and 23 of the casing 2, and it includes a projected rim part 51 provided along the longitudinal direction in an inner surface of each of the left and right side wall parts 22 and 23, two notch portions 52 provided along the longitudinal direction in side peripheral surfaces of the rod lens 4, a concave groove 53 provided along the longitudinal direction above the projected rim part 51 in the inner surface of each of the left and right side wall parts 22 and 23, and an elastic body 54 detachably provided in each of the concave grooves 53.

Especially, as shown in FIG. 3, each projected rim part 51 is provided to be projected inward from the inner surface and extending over from one end to the other end in the longitudinal direction of each of the left and right side wall parts 22 and 23, and it includes an upwardly facing surface 51a which is a generally horizontal plane and an inward surface 51b which is a plane generally perpendicular to the upwardly facing surface 51a. Further, the two projected rim parts 51 provided in the respective left and right side wall parts 22 and 23 have the same shape laterally symmetrical with respect to the optical axis C2. In addition, a distance between the upper side portions above the projected rim parts 51 in the pair of left and right side wall parts 22 and 23 is configured to be larger than the outer diameter of the rod lens 4 and configured to be able to accommodate the rod lens 4 from an upper opening of the casing 2. Thus, the accommodating work of the rod lens 4 into the casing 2 is facilitated.

Especially, as shown in FIG. 3, each notch potion 52 is formed to extend over from one end to the other end in the longitudinal direction in each of the side peripheral surfaces of the rod lens 4, and it includes a downwardly facing surface 52a which is a plane contacting with the upwardly facing surface 51a of the projected rim part 51 and an outward surface 52b which is a plane generally perpendicular to the downwardly facing surface 52a. The two notch portions 52 formed in the rod lens 4 have the same shape laterally symmetrical with respect to the optical axis C2.

And a distance between the inward surfaces 51b of the two projected rim parts 51 is generally identical to the distance between the outward surfaces 52b of the two notch portions 52, and the inward surfaces 51b of the projected rim parts 51 are in contact with the outward surfaces 52b of the notch portions 52 in a state that the upwardly facing surfaces 51a of the projected rim parts 51 are in contact with the downwardly facing surfaces 52a of the notch portions 52. Thus, the rod lens 4 can be positioned with respect to the casing 2 in the vertical direction as well as in the horizontal direction. That is, the optical axis C1 of each LED 31 on the LED substrate 3 positioned in the lateral direction with respect to the casing 2 coincides with the optical axis C2 of the rod lens 4 positioned in the lateral direction with respect to the casing 2.

The concave groove 53 is provided along the longitudinal direction above the projected rim part 51 to extend over from one end to the other end in the longitudinal direction in the inner surface of each of the left and right side wall parts 22 and 23. This concave groove 53 is formed in a manner such that the elastic body 54 is fit thereto in a state that the downwardly facing surface 52a of the notch portion 52 is in contact with the upwardly facing surface 51a of the projected rim part 51 and is formed in a position where the elastic body 54 contacts with the side peripheral surface of the rod lens 4.

In the present embodiment, the elastic bodies 54 are a linear tubes having resilience which are detachably provided in respective concave grooves 53 and which are excellent in heat resistance and corrosion resistance. These elastic bodies are fit to each concave groove 53 in a state that the downwardly facing surface 52a of each notch portion 52 is in contact with the upwardly facing surface 51a of each projected rim part 51 and is brought into contact with each side peripheral surface of the upper side portion above the respective notch 52 in the rod lens 4 to thereby press the respective notch portion 52 to the corresponding projected rim part 51.

Figure 4A:
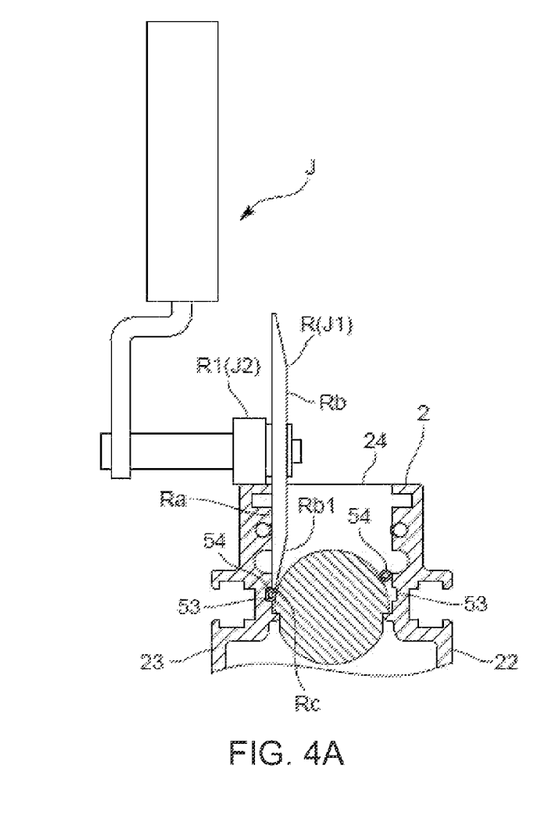
FIGS. 4A-4B are schematic diagrams showing an inserting process of an elastic body of the same embodiment.
Figure 4B:
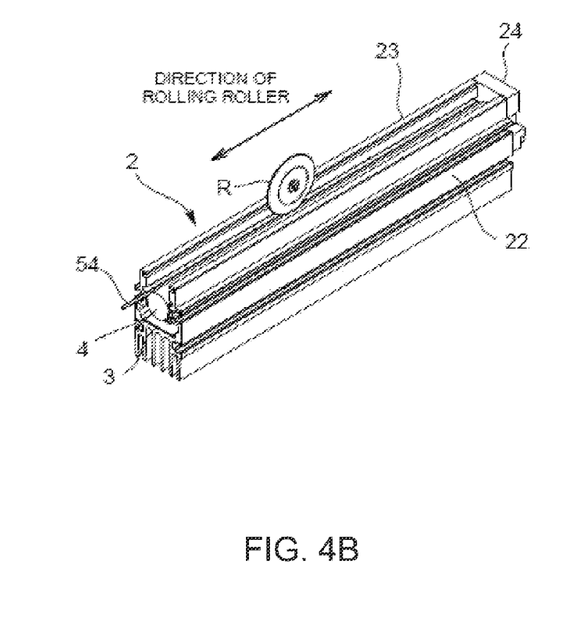

Next, an assembling procedure of the line light irradiation device 100 configured like this is described referring to FIGS. 4A-4B.

First, after accommodating the LED substrate 3 in the casing 2 which has been pultrusion-molded or extrusion-molded and subjected to a prescribed process for fixing the front and rear side walls 24 and 25 to both end portions, the rod lens 4 is accommodated from, for example, an upper part opening of the casing 2 (lens accommodating process). In this state of accommodating the rod lens 4 in the casing, the notch portions 52 of the rod lens 4 and the projected rim parts 51 of the casing 2 are brought into contact with each other, whereby the rod lens 4 is vertically and laterally positioned with respect to the casing 2. It is noted that, in FIG. 4A-4B, shown is a case where the front side wall 24 is attached to the left and right side walls 22 and 23 of the casing 2 in a step of accommodating the LED substrate 3 and rod lens 4.

Then, the silicon tubes 54 serving as the two elastic bodies are fit into the concave grooves of the left and right side walls 22 and 23 (elastic body fitting process). In this fitting work, after the silicon tube 54 is arranged in a gap between the upper end portion of each concave groove 53 and the side peripheral surface of the rod lens 4, the silicon tube 54 is fitted into each of the concave grooves 53 using a jig.

Here, the jig J includes a jig main body J1 having a tip surface which contacts with the silicon tube 54 and a guide part J2 provided in the jig main body J1 and contacting with the upper surface of the casing 2. Specifically, the jig main body J1 is a main body roller R rotatable about a rotation axis, and the guide part J2 is a guide roller R1 provided coaxially with the rotation axis of the main body roller R. The main body roller R has its one side surface Ra forming a plane shape and the other side surface Rb including a tapered surface Rb1. Further, the guide roller R1 contacts with the upper surface of the casing 2, whereby a position of a side peripheral end surface Rc of the main body roller R is rendered to be a fitting position where the silicon tube 54 is fit to the concave groove 53.

Then, in a state that one of the side surface Ra of the main body roller R is along the inner side surface of the casing 2, by rolling the guide roller R1 being in contact with the upper surface of the casing 2, the side peripheral end surface Rc which is a tip surface of the main body roller R contacts with the silicon tube 54 and the silicon tube 54 can be fit into the concave groove 53 by pressing in the silicon tube 54 from the upper portion. Further, since the other side surface Rb of the main body roller R has a tapered surface Rb1, the main body roller R does not contact with the side peripheral surface of the rod lens 4 in the fitting process of the silicon tube 54. Thus, the silicon tube 54 is fit to the concave groove 53, and the notch portion 52 of the rod lens 4 is pressed to be in a state of being fixed to the projected rim part 51 of each of the left and right side wall parts 22 and 23 by an elastic return force thereof. Here, the shortest distance (a code "d" in FIG. 3) between the upper end portion of the concave groove 53 and the side peripheral surface of the rod lens 4 is set to be smaller than the outer diameter of the silicon tube 54 in a natural state (in a state of not being deformed by an external force). Thus, the silicon tube 54 fit to the concave groove 53 is prevented from being detached from the concave groove 53. Here, the guide roller R1 is attached to the roller R, and by contacting this guide roller R1 with the upper surface of each of the side wall parts 22 and 23 and rolling the roller R along the inner surface of each of the side wall parts 22 and 23, the tip portion of the roller R presses the silicon tube 54 into the concave groove 53.

Moreover, in the assembling step, the silicon tube 54 is partly rendered to protrude to a side of the front side wall 25. And the protruded portion is pulled outward in the longitudinal direction and a proximal portion of the protruded portion is cut off. Thus, the silicon tube 54 in the concave groove 53 shrinks inward in the longitudinal direction and is rendered to be coplanar with the end surface of the rod lens 4 or enter inside thereof. Thus, when the rear side wall 25 is fixed to each of the left and right side walls 22 and 23, the silicon tube 54 is prevented from becoming an obstacle.

And after fitting the silicon tube 54 to fix the rod lens 4, the light transmission plate 6 is slid to be attached to the slide groove 7, and thereafter the rear side wall 25 is fixed to each of the left and right side walls 22 and 23 with screws to thereby assemble the line light irradiation device 100.

Effect of the Present Embodiment

According to the line light irradiation device 100 according to the present embodiment configured like this, the fixing mechanism 5 includes the projected rim part 51 provided in the inner surface of each of the left and right side wall parts 22 and 23 and the notch portion 52 provided in the side peripheral surface of the rod lens 4, and by contacting between these upwardly facing surface 51a and the downwardly facing surface 52a, the rod lens 4 can be fixed to the casing 2 while positioning the rod lens 4 to the casing 2 in the vertical direction.

Further, since the fixing mechanism 5 includes the concave groove 53 and the elastic body 54 which is fitted to this concave groove 53 to press the side peripheral surface of the rod lens 4, the rod lens 4 can be fixed to the casing 2 while preventing looseness of the rod lens 4 to the casing 2.

Furthermore, the contact between the casing 2 and the rod lens 4 is performed only between the upwardly facing surface 51a of the projected rim part 51 and the downwardly facing surface 52a of the notch portion 52, and even though the rod lens 4 is moved by sliding in the longitudinal direction, a light transmission portion of the rod lens 4 is not damaged.

Moreover, after contacting the downwardly facing surface 52a of the notch portion 52 with the upwardly facing surface 51a of the projected rim part 51, the rod lens 4 can be fixed by pressing to the casing 2 only by fitting the elastic body 54 to the concave groove 53, and therefore the assembly can be facilitated. At this time, since the elastic body 54 is not fitted to the concave groove 53 at the time of attaching the rod lens 4 to the casing 2, the attachment work of the rod lens 4 to the casing 2 can be facilitated.

In addition, since the casing 2 is integrally formed, not only the number of assembling man-hours can be reduced but also heat dissipation performance of the casing 2 can be improved. Moreover, only the notch portion 52 is provided in the rod lens 4, and it is sufficient to merely process the rod lens, such as by cutting, and therefore the processing is easy and a manufacturing cost can also be lowered.

Figure 5:
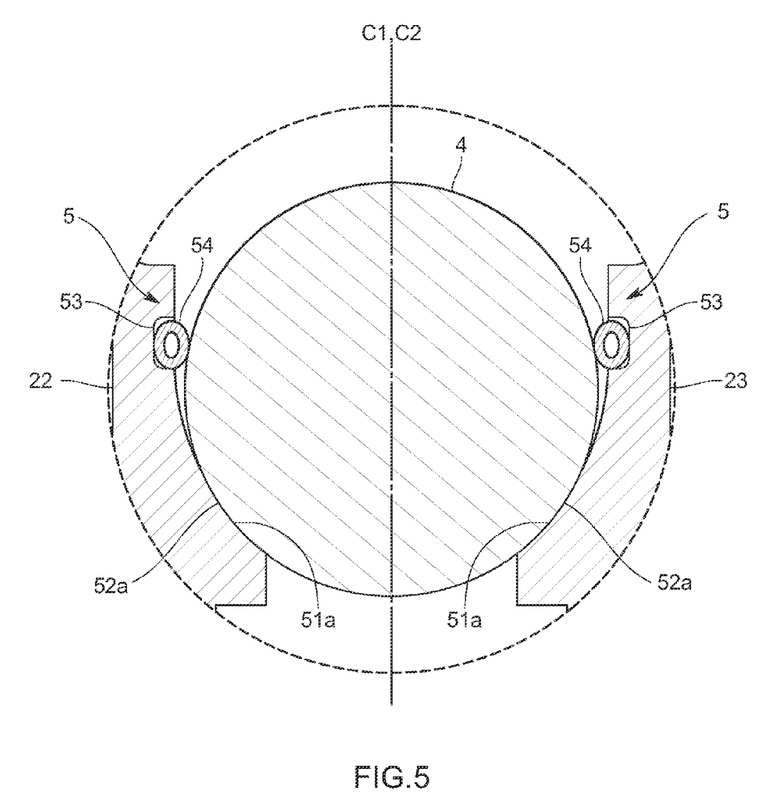
FIG. 5 is a partially expanded sectional view of a line light irradiation device of a modified embodiment.

It is noted that the present invention is not limited to the above embodiment. For example, as shown in FIG. 5, the rod-like lens may be the rod lens 4 having no notch portion. In this case, the upwardly facing surface 51a is provided in the inner surface of each of the left and right side walls 22 and 23 and is a curved surface having a curvature corresponding to the side peripheral surface of the rod lens 4. Also, the downwardly facing surface 52a is formed of the side peripheral surface in the lower side of the rod lens 4.

Figure 6:
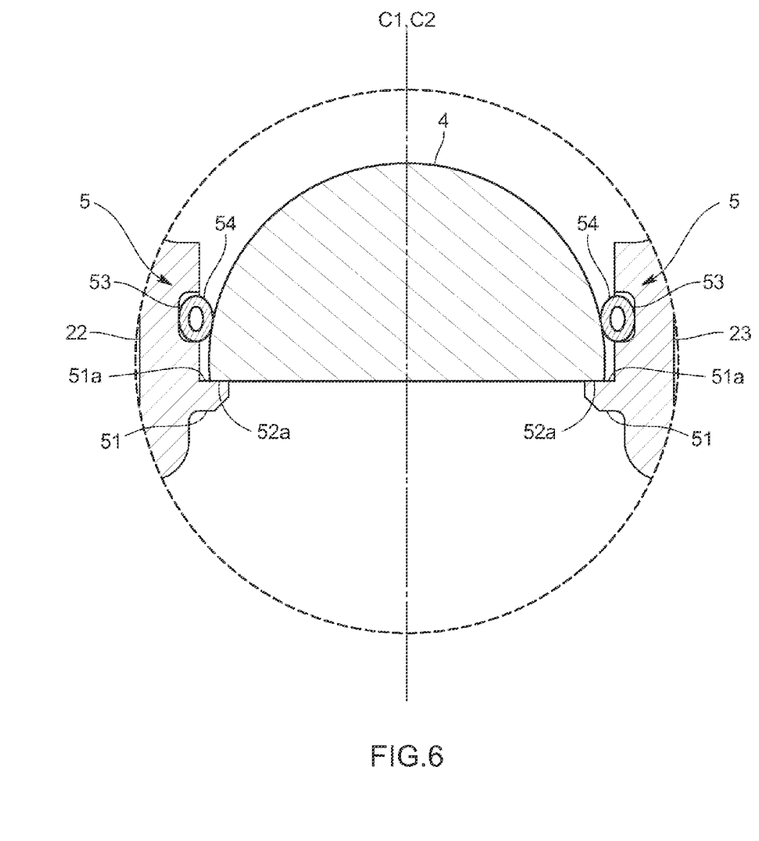
FIG. 6 is a partially expanded sectional view of a line light irradiation device of a modified embodiment.

Further, as shown in FIG. 6, the rod-like lens may be a cylindrical lens having a semicircular shape in section. In this case, the upwardly facing surface 51a is formed of a generally horizontal upper surface of the projected rim part 51 provided in the inner surface of each of the left and right side walls 22 and 23. Also, the downwardly facing surface 52a is formed of each of the left and right end portions of the lower surface of the cylindrical lens 4.

Figure 7:
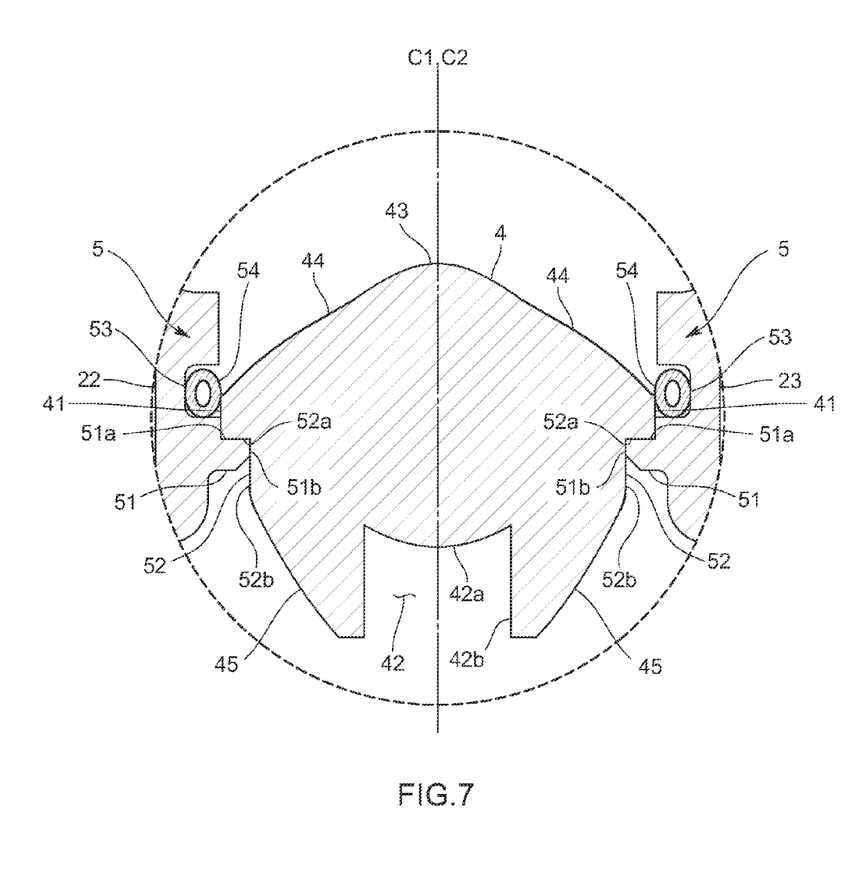
FIG. 7 is a partially expanded sectional view of a line light irradiation device of a modified embodiment.

Furthermore, as shown in FIG. 7, the rod-like lens 4 may have a projected rim part 41 in each of left and right side portions along the longitudinal direction. In this case, the upwardly facing surface 51*a* is formed of a generally horizontal upper surface of the projected rim part 51 provided in the inner surface of each of the left and right side walls 22 and 23. Also, the downwardly facing surface 52*a* is formed of each of a generally horizontal lower surface of the projected rim part 41 of the rod-like lens 4. Further, the inward surface 51*b* is formed of an upper part side surface of the projected rim part 51 in each of the left and right side walls 22 and 23, and the outward surface 52*b* is formed of a side surface in the lower part of the projected rim part 41 in the rod-like lens 4. It is noted that this rod-like lens 4 has an equal shape in section in the longitudinal direction and a concave portion 42 is opened for accommodating the LEDs. A bottom surface 42*a* of this concave portion 42 is formed to have a convex lens shape expanded toward the proximal side and a side surface 42*b* is substantially parallel to an optical axis. Meanwhile, a central convex lens part 43 is formed in a tip surface of the lens 4 by expanding the central portion thereof, and left and right convex lens part 44 of a different curvature therefrom are formed in both left and right sides of this central convex lens part 43. Further, in the side surface of the lens 4, there is provided a curved expanding surface 45 that is a reflection element formed to have an outline in a parabola in section.

In addition, the present invention should not be limited to the above embodiments and since it will be understood that various modifications can be made unless departing from the spirit of the invention.

INDUSTRIAL APPLICABILITY

By the present invention, a lens can be fixed to a casing and not only looseness thereof can be prevented but also an assembly can be facilitated.

The invention claimed is:

1. A line light irradiation device comprising:
    an integrally molded casing having a bottom wall part extending in a longitudinal direction and a pair of side wall parts extending upward from both sides in the longitudinal direction of the bottom wall part;
    an LED substrate provided on the bottom wall part of the casing;
    a rod-shaped lens provided above the LED substrate along the longitudinal direction inside the casing; and
    a fixing mechanism for fixing the lens to the pair of side wall parts,
    wherein the fixing mechanism comprises:
    a respective upwardly facing surface extending in the longitudinal direction along an inner surface of each of the side wall parts;
    a respective downwardly facing surface extending in the longitudinal direction along each side peripheral surface of the lens;
    a respective concave groove extending along the longitudinal direction above the upwardly facing surface on the inner surface of each of the side wall parts; and
    a respective elastic body detachably provided in each concave groove and fitting into each concave groove to be in contact with a corresponding side peripheral surface of the lens in a state that the downwardly facing surfaces are in contact with the upwardly facing surfaces to thereby press the downwardly facing surfaces against the upwardly facing surfaces.

2. The line light irradiation device according to claim 1, wherein a shortest distance between an upper end portion of each concave groove and the corresponding side peripheral surface of the lens is smaller than a width size in a natural state of the elastic body.

3. The line light irradiation device according to claim 1, wherein each upwardly facing surface is formed of an upper surface of a respective projected rim part extending in the longitudinal direction on the inner surface of each of the side wall parts, and
    each downwardly facing surface is formed of a respective lower surface of each of associated two notch portions which are provided along the corresponding side peripheral surface of the lens and symmetrically formed with respect to an optical axis.

4. The line light irradiation device according to claim 3, wherein each projected rim part has an inward surface which is substantially perpendicular to the upwardly facing surface,
    each notch portion has an outward surface which is substantially perpendicular to the downwardly facing surface, and
    the upwardly facing surface of each projected rim part is in contact with the downwardly facing surface of the corresponding notch portion in a state that the inwardly facing surface of the projected rim part is in contact with the corresponding outwardly facing surface of the notch portion.

5. The line light irradiation device according to claim 3, wherein a space between upper side portions above the projected rim parts of the pair of side wall parts is configured to be larger than an outer diameter of the lens.

6. A manufacturing method of the line light irradiation device according to claim 1 comprising:
    a lens accommodation process of accommodating the lens in the casing; and
    an elastic body fitting process of fitting the elastic body into the concave groove after the lens accommodation process.

7. The manufacturing method according to claim 6, wherein the elastic body fitting process fits the elastic body into the concave groove using a jig after the elastic body fitting process arranges the elastic body in a gap between the upper end portion of the concave portion and the side surface of the lens.

8. The manufacturing method according to claim 7, wherein the jig includes a jig main body having a tip surface which is in contact with the elastic body, and a guide part which is provided in the jig main body and to be in contact with an upper surface of the casing, and
    by bringing the guide part into contact with the upper surface of the casing, the tip surface of the jig main body is in contact with the elastic body to thereby fit the elastic body into the concave groove.

9. The manufacturing method according to claim 8, wherein the jig main body is a main body roller which is rotatable about a rotation axis,
    the guide part is a guide roller coaxially provided with the rotation axis of the main body roller;
    by rolling the guide roller while contacting with the upper surface of the casing in a state that one side surface of the main body roller is along an inner side surface of the casing, a side peripheral end surface of the main body roller is in contact with the elastic body to thereby fit the elastic body into the concave groove.

\* \* \* \* \*